United States Patent [19]

Carlsson et al.

[11] Patent Number: 5,716,639
[45] Date of Patent: Feb. 10, 1998

[54] LIPOPHILIC CARRIER PREPARATIONS

[75] Inventors: Anders Carlsson; Bengt Herslöf, both of Stockholm, Sweden

[73] Assignee: Scotia LipidTeknik AB, Stockholm, Sweden

[21] Appl. No.: 676,137

[22] PCT Filed: Feb. 6, 1995

[86] PCT No.: PCT/SE95/00117

§ 371 Date: Jul. 15, 1996

§ 102(e) Date: Jul. 15, 1996

[87] PCT Pub. No.: WO95/20945

PCT Pub. Date: Aug. 10, 1995

[30] Foreign Application Priority Data

Feb. 4, 1994 [SE] Sweden ............................ 9400368
Jul. 12, 1994 [SE] Sweden ............................ 9402456

[51] Int. Cl.[6] .................... A61K 9/127; A61K 31/22; A61K 31/225
[52] U.S. Cl. .................... 424/450; 514/546; 514/547; 514/548; 514/549
[58] Field of Search .................... 514/546, 547, 514/548, 549; 424/450

[56] References Cited

U.S. PATENT DOCUMENTS

| | | | |
|---|---|---|---|
| 4,610,868 | 9/1986 | Fountain et al. | 424/1.1 |
| 5,151,272 | 9/1992 | Engstrom et al. | 424/450 |
| 5,234,767 | 8/1993 | Wallach et al. | 428/402.2 |

FOREIGN PATENT DOCUMENTS

| | | |
|---|---|---|
| 0 009 842 | 4/1980 | European Pat. Off. . |
| 0 249 561 | 12/1987 | European Pat. Off. . |
| 6-009675 | 1/1994 | Japan . |
| 9205771 | 4/1992 | WIPO . |

OTHER PUBLICATIONS

1. Foley et al., "Permeability of Liposomes Composed of Binary Mixtures of Monogalactosyldiaclglycerol and Digalactosyldiacglycerol", *Chemical Abstracts*, 108, 200519 (1988).

*Primary Examiner*—Kevin E. Weddington
*Attorney, Agent, or Firm*—Hoffmann & Baron, LLP

[57] ABSTRACT

The invention relates to a lipophilic carrier preparation having a continuous lipid phase, comprising a polar lipid material in combination with a non-polar lipid, and optionally a polar solvent, wherein the polar lipid material is a galacto-lipid material. The invention also relates to the use of said lipophilic carrier preparation as a carrier for an active substance in a pharmaceutical composition, but also in nutritional, cosmetical and food products, as well as to a pharmaceutical composition.

The invention relates to a lipophilic carrier preparation having a continuous lipid phase, comprising a polar lipid material in combination with a non-polar lipid, and optionally a polar solvent, wherein the polar lipid material is a galactolipid material. The invention also relates to the use of said lipophilic carrier preparation as a carrier for an active substance in a pharmaceutical composition, but also in nutritional, cosmetic and food products, as well as to a pharmaceutical composition.

18 Claims, No Drawings

LIPOPHILIC CARRIER PREPARATIONS

This application is a 371 of PCT/SE 95/00117 filed Feb. 6, 1995.

TECHNICAL FIELD

This invention relates to lipophilic carrier preparations having a continuous lipid phase, comprising a polar lipid material, in combination with a non-polar lipid and optionally a polar solvent. Said carrier preparation is suitable for use as a carrier for active materials in pharmaceutical compositions, as well as in cosmetical, food and agricultural products.

BACKGROUND OF THE INVENTION

It is a general problem in the pharmaceutical industry to incorporate drugs into lipophilic carriers which are biocompatible and well tolerated by humans. The reason for this is, firstly, the wide range of chemical structures, and therefore properties, of the active components which art to be incorporated, and, secondly, a suitable carrier based on ingredients which makes the carrier sufficiently flexible to incorporate active components with the mentioned wide range of structural variations.

In order to create flexible lipophilic carriers, polar lipids need to be employed, preferably natural membrane lipids for the sake of biocompatibility and safety, and combined with non-polar lipids, such as vegetable oils or sterol esters. At present time the only membrane lipids available are phospholipid materials, mainly derived from soy or egg lecithin or made by synthetic routes. The phospholipids are zwitter-ionic, such as phosphatidylcholine and phosphatidylethanolamine, or negatively charged, such as phosphatidylinositol or phosphatidylglycerol.

Lipophilic carriers may be organised solutions, such as microemulsions or reverse micellar solutions, reverse vesicles or water-in-oil emulsions.

Margarines and spreads are water-in-oil emulsions which may contain as much as 75% by weight of an aqueous phase. The aqueous phase is dispersed in a triglyceride oil, typically a vegetable oil such as rapeseed oil. The aqueous phase normally contains a thickening agent, such as gelatine in order to stabilise the water-rich oil-continuous emulsion. The emulsifier is typically a phospholipid such as soybean phospholipids (soy lecithin). These emulsifiers consist of mixtures of phospholipid classes, such as phosphatidylcholine and phosphatidylethanolamine, which are zwitter-ionic, and phosphatidylinositol, which is ionic. It is a common knowledge that these lecithin emulsifiers are the most utilized natural lipids in preparing stable food emulsions on an industrial scale. It is also well-known that such emulsions suffer from disadvantages and problems which relate to the lecithin emulsifier.

PRIOR ART

There are only a few examples on lipophilic preparations having a continuous lipid phase reported.

WO 92/05771 describes a lipid particle forming matrix of at least two lipid components; one is non-polar and another is amphiphatic and polar. This particle forming matrix, which can contain bioactive materials, spontaneously forms discrete lipid particles when interacting with aqueous systems. The amphiphatic and polar lipid components are said to be bilayer forming and are chosen from phospholipids such as phosphatidylcholine; the non-polar lipids are mono-, di- or triglycerides.

Microemulsion gels comprising lecithin, i.e. phosphatidylcholine, have been described and characterized by P. L. Luisi, see e.g. D. Capitani et al., *Langmuir*, 1993, Vol. 9, pp. 685–689. Besides the phospholipid, these gels are composed of a small amount of water and an organic solvent, such as alkanes, fatty acid esters and amines. They are also referred to as organogels. The gels may be used as a matrix for transdermal transport of drugs.

The presence of reverse vesicles, the counter structures to normal vesicles, in an oil was first reported by H. Kunieda, see e.g. H. Kunieda et al., Advanced Materials, 1992, Vol. 4, pp. 291–293. Reverse vesicles are a dispersion of lamellar liquid crystal, which swells a considerable amount of oil, i.e. the vesicles consist of reverse bilayer structures. The reverse bilayers are normally composed of a mixture of hydrophilic and lipophilic amphiphiles.

Glycosylglycerides are a type of glycolipids which are well-known constituents of plant cell membranes. Two types based on galactose are very common, monogalactosyldiacylglycerol, MGDG, and digalactosyldiacylglycerol, DGDG, representing up to 40% of the dry weight of the thylakoid membranes.

Plant glycolipids have carbohydrate units, mainly of galactose, linked to glycerol. In MGDG the 1-position of the galactose ring has a β-link to glycerol, and in DGDG there is an α, 1–6 bond between the sugars. A minor constituent is the plant sulpholipid, more correctly named sulphoquinovosyldiacylglycerol, DQDG, which contains a sulphonate rather than a hydroxyl group linked to carbon 6 of the terminal deoxyglucose residue. Most plant glycolipids can be described by the general formula

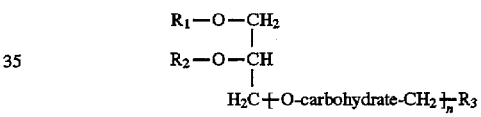

wherein $R_1$ and $R_2$ independently of each other are saturated or unsaturated fatty acid residues of 2–24 carbon atoms and 0–6 double bonds, further esterified hydroxyacids, that is estolides, or hydrogen; the carbohydrate is a monosaccharide unit; n=1–5; and $R_3$ is a hydroxyl or sulphonate group.

SE 9400368-8 discloses an industrially applicable process for preparing glycosylglycerides from plants, preferably cereals, by means of extraction and chromatographic separations.

In investigating the interaction of the glycosylglycerides with non-polar lipids, such as mono-, di- and triglycerides, fatty alcohols and acids, sterols and sterol esters, optionally combined with other polar lipids such as phospholipids and sphingolipids, without water, or with only small amounts of water, we have surprisingly found a behaviour which makes such preparations suitable as lipophilic carriers for drugs, but also as formulations for skin care, nutrition and food.

DESCRIPTION OF THE INVENTION

The present invention provides lipid carriers based on galactolipids, which is a polar lipid material, in combination with non-polar lipids. The polar headgroups of the galactolipids are galactose units, which have quite different physicochemical properties compared to the phospholipids. Thus, the incorporation mechanisms are based on interactions of the hydroxyl groups of the polar headgroup, i.e. the galactose unit, and the lipophilic chains of the galactosylacylglycerols and the non-polar component, with the compound which is to be incorporated.

The invention relates to a lipophilic carrier preparation having a continuous lipid phase, comprising a non-polar lipid in combination with a polar lipid material, and optionally a polar solvent, characterised in that the polar lipid material is a galactolipid material consisting of at least 50% digalactosyldiacylglycerols, the remainder being other polar lipids.

In a preferred preparation the galactolipid material consists of about 70–80% digalactosyldiacylglycerols and 20–30% other polar lipids.

In another preferred preparation the galactolipid material consists of up to 100% digalactosyldiacylglycerols.

The digalactosyldiacylglycerols can be described by the general formula

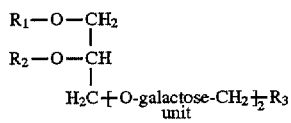

wherein $R_1$ and $R_2$ independently of each other are saturated or unsaturated fatty acid residues of 10–22 carbon atoms and 0–4 double bonds, or hydrogen; and $R_3$ is a hydroxyl or sulphonate group.

As preferred examples of fatty acid residues $R_1$ and $R_2$ can be mentioned naturally occurring fatty acyl groups, such as residues from the saturated acids palmitic ($C_{15}H_{31}CO$: 16:0) and stearic acid ($C_{17}H_{35}CO$; 18:0); from the monounsaturated acid oleic acid ($C_{17}H_{33}CO$: 18:1); and from the polyunsaturated acids linoleic ($C_{17}H_{31}CO$: 18:2) and linolenic acid ($C_{17}H_{29}CO$; 18:3). The fatty acid residues can also contain hydroxy acids linked to the glycerol moiety with their hydroxyl groups esterified by further fatty acids, so called estolides.

The other polar lipids being part of the galactolipid material are a mixture of different glyco- and phospholipids, such as MGDG and phosphatidylcholines. The composition depends on the starting material and process used for the manufacture of the galactolipids.

The specific proportions of the components of the galactolipid material are not critical to the present invention as long as the content of DGDG is at least 50%. For many applications, however, the maximum benefits are realised by a high content of DGDG, the most important bilayer-forming component.

The galactolipid material can be extracted from almost any kind of plant material. Preferred plant materials are seeds and kernels from grains and cereals, for instance wheat, rye, oats, corn, rice, millet and sesame. Oat groats as well as wheat gluten have a high lipid concentration and are therefore of advantage to use in the preparation process.

Synthetic diglycosyldiacylglycerols based on galactose or any other monosaccharide unit, such as glucose, and natural glycosylglycerides, isolated from any source, based on other carbohydrate units than galactose, such as glucose, can be used in accordance with the invention.

No particular limitation is imposed on the non-polar lipid material. Vegetable oils, animal oils, synthetic oils, fatty acids, natural and synthetic glycerides, sterol esters, fatty alcohols, etc. may be mentioned by way of example.

All types of lipophilic organised solutions were surprisingly possible to obtain by using galactolipids. The incorporated active materials may be part of the organised solutions or stabilised by these in the form of, for example, suspensions.

By way of example, a lipophilic carrier preparation can be obtained by mixing the galactolipids with a non-polar lipid, such as a triacylglycerol. The triacylglycerol may be selected from palm oil or natural oils with similarly, relatively high solid fat content or melting range. Preferred and suitable triacylglycerols are palm oil fractions, obtained by fractionating commercial palm oil into specific mixtures of triacylglycerols, based on the combination of mainly palmitic, oleic and stearic esters of glycerol.

A lipophilic carrier preparation can also be obtained by mixing the glycosylglycerides with liquid triglyceride oils, such as medium-chain triacylglycerol (MCT) and soybean oil.

In addition, the non-polar lipid-galactolipid mixture can contain increasing contents of water or aqueous solution which can lead to the formation of reverse vesicles, reverse micelles and water-in-oil emulsion.

Reverse vesicles are prepared by adding a mixture of galactolipids and a more polar amphiphile, such as lysophosphatidylcholine, in a ratio of 4:1 by weight, to a triglyceride oil, preferably MCT oil. The total concentration of amphiphiles is less than 3% (w/w). A small amount of water or aqueous solution, less than 1% (w/w) of the total preparation, is then added. After ultrasonication, a fine dispersion of reverse vesicles is obtained.

At higher glycolipid concentrations, but still low water content, 0.5–2% (w/w) of the total preparation, reverse micelles can be prepared. Reverse micelles, also called microemulsions, consist of water aggregates in an oil. Reverse micelles are thermodynamically stable. The shape and structure of the aggregates may lead to viscous systems, "microemulsion gels".

At still higher water contents, >5% (w/w) of the total preparation, water-in-oil emulsions are formed. These are two-phase systems, consisting of finely dispersed water droplets in an oil. Water-in-oil emulsions are thermodynamically unstable, but may be kinetically stable.

The aqueous solution can consist of pure water, buffer solution, saline, solutions of glucose, galactose, propylene glycol, polyethylene glycols, glycerol, etc. In addition, thickening agents such as gelatine, agarose, carrageenan, methyl cellulose and ethyl hydroxyethyl cellulose may be employed.

The invention also refers to the use of a lipophilic carrier preparation as described, as a carrier for an active substance in a pharmaceutical, cosmetical, food or agricultural product.

The invention also refers to a pharmaceutical composition comprising a lipophilic carrier preparation as described, in combination with a bioactive substance.

The invention also refers to a pharmaceutical composition comprising a lipophilic carrier preparation as described, wherein the non-polar lipid is an MCT oil, evening primrose oil, a palm oil fraction, or a bioactive substance.

The bioactive substance can be a lipophilic drug such as anti-cancer agents, anti-microbial and particularly anti-fungal agents, immunosuppressant drugs like cyclosporin, dermatological drugs, such as analgesic and antipholgistic agents, antipruritics, disinfectants, astringents, emollients, and hormones, psychotropic drugs, anaestethic drugs and other drugs which are lipophilic and which may present formulation problems which could be solved by the use of galactolipids. There are also many lipids such as free fatty acids, mono-, di- and triacylglycerols, phospholipids, cholesterol esters and lipids of many other types which have therapeutic actions in themselves and which may be advantageously formulated in the form of an lipophilic carrier, based on the galactolipids. In this case the bioactive substance is the non-polar lipid.

A pharmaceutical and cosmetic preparation can be prepared by melting a palm oil fraction in an open water bath at a temperature range of 40°–70° C. The active ingredients and the glycosylglycerides are weighed in a vial. The melted palm oil fraction is transferred to the vial and the mixture is dispersed with a high shear mixer at approximately 1000 rpm and at temperature range of 40°–70° C. for 2–4 min. The amount of water or aqueous solution required to form a topically applicable formulation is added and the formulation is mixed carefully with a rod.

The pharmaceutical composition may be formulated for oral, enteral, parenteral, rectal, vaginal, topical, ocular, nasal or aural administration to animals, especially mammals, including humans.

Topical skin care preparations may be classified roughly in medicinal topical skin care preparations and cosmetological preparations in accordance with their manner of use.

As exemplary medicinal topical skin care preparations, may be mentioned various ointments containing one or more active ingredients. Ointments include both those containing an oily base and those containing an oil-in-water or water-in-oil emulsion-type base.

Where used as a cosmetic preparation, it is possible to mix in addition to the essential ingredients those employed routinely as cosmetological ingredients such as oily substance, ultraviolet absorbent, alcohol, chelating agent, pH regulator, antiseptic, thickening agents, pigment, perfume base and the like in combination as needed.

As cosmetics, skin cosmetological preparations of various forms may be formulated including, for example water-in-oil or oil-in-water type emulsified cosmetics, creams, cosmetological emulsions, toilet waters, oily cosmetics, lipsticks, foundations, skin cleansing preparations, hair tonics, hair styling preparations, hair grooming preparations, hair growth stimulants, etc.

Water-in-oil emulsions, e.g. margarines and spreads, are prepared by conventional methods.

GALACTOLIPID MATERIAL

Galactolipid materials have been prepared from different cereals as stated below, and used for making carrier preparations and pharmaceutical compositions of the invention as stated in the examples. In the specification % refers to % by weight if not otherwise stated. The proportion of the solvents in solvent mixtures is given in parts by volume.

GALACTOLIPID MATERIAL FROM OATS 200 kg of oat kernels (Kungsörnen AB, Sweden) were ground and extracted with 1000 l of 95% ethanol at 70° C. for 3 h in an extraction tank under stirring. The slurry was centrifuged while still warm and separated from solid particles. The liquid fraction was evaporated at 60° C. which gave about 10 kg of a light brown oil.

The oil was applied to a stainless steel column containing 6.25 kg of silica gel (Matrex Silica Si, particle size 20–45 mm, pore diameter 60 Å, from Amicon Corp., USA). The column temperature was 50° C. The column was then washed with 30 l of a mixture of hexane:isopropanol, 90:10, in order to remove all nonpolar lipids.

The galactolipid material was then eluted from the column with 20 l of a mixture hexane:isopropanol, 60:40, giving a galactosyldiacylglycerol fraction. Evaporation of this fraction gave about 700 g of DGDG, the major lipid class. The galactolipid material was then dispersed in water and subjected to freeze-drying, which resulted in a free-flowing powder.

ENRICHMENT OF DGDG FROM GALACTOLIPIDS 50 g galactolipids from oats, as obtained above, having a content of DGDG of about 70%, were dissolved in 250 ml hexane: isopropanol, 70:30, giving a total amount of 300 ml. the solution obtained was loaded on a silica gel (110 g) column and the less polar constituents were eluted with 1 l of the mixture of hexane:isopropanol, 70:30. The enriched DGDG fraction was eluted with 2 l acetone. The acetone fraction was evaporated and freeze-dried. The total yield was 17 g of an almost pure DGDG product.

HYDROGENATION OF GALACTOLIPIDS 200 g of a galactolipid mixture obtained from oats as stated above was dissolved in 2 l warm isopropanol. 15 g of a palladium on carbon catalyst (Pd 15%, moisture 53%, Engelhard Rome s.r.i., Italy) was placed in the bottom of a pressure reactor (Model No. 4552M; Parr Instrument Co., USA) equipped with two impellers on a stirrer shaft. The solution was then transferred into the reactor under a seal of nitrogen to reduce the fire hazard. The reactor vessel was sealed and first pressurized three times with nitrogen in order to remove air and then three times with hydrogen gas (Plus 4.5, from AGA Gas AB, Sweden). The hydrogen pressure was then kept at 6 bars, the stirrer set at 600 rpm and the mixture was heated to 70° C. It took 14 minutes for the reaction mixture to reach its temperature setpoint. The hydrogenation process was conducted for 6 hours after which the reaction product was filtered through a 0.45 µm filter in order to remove carbon particles and palladium. Solvent was evaporated on a rotavapor, the residual solid material was dispersed in 1600 ml of deionized water and freeze-dried.

The yield of hydrogenated galactolipids after filtration and freeze-drying was 155 g. The hydrogenation performance was evaluated by gas chromatography; only saturated fatty acids could be detected in the hydrogenated product.

GALACTOLIPIDS FROM WHEAT GLUTEN 1 kg of wheat gluten powder (AB Skanebrännerier, Sweden) was extracted with 4 l of 95% ethanol at 70° C. for 3 h in a beaker. The slurry was then filtered under a pressure of 400–500 kPa and the filtercake obtained was washed with 1 l of warm 95% ethanol. The combined ethanol solutions were evaporated at maximum 60° C. and gave about 60 g of a yellow oil.

The oil was applied to a stainless steel column containing 45 g of silica gel (Matrex Silica Si, particle size 20–45 µm, pore size 60 Å, from Amicon Corp., USA). The column was then washed with 700 ml of a mixture hexane:isopropanol, 90:10, in order to remove neutral lipids.

In order to remove MGDG and some other polar lipids the column was subsequently washed with 1000 ml of a mixture hexane: isopropanol, 70:30. Elution of DGDG was carried out with 1000 ml of pure acetone. After evaporation about 4 g of an almost pure DGDG product was obtained.

GALACTOLIPIDS FROM RYE 100 g rye flakes (Kungsörnen AB, Sweden) were stirred for 60 min in a mixture of industral hexane and isopropanol, 90:10. The slurry was filtered and evaporated which gave 0.5 g polar lipids. The residue, dissolved in 10 ml of a mixture of hexane and iso-propanol, 70:30, was loaded on three Sep-pak Silica plus columns (millipore Corp., USA) connected in series, washed with 20 ml of the same mixture of solvents and eluted with 15 ml acetone. The eluate was evaporated and freeze-dried and the yield was 47 mg of galactolipids.

CHEMICAL AND PHYSICAL CHARACTERISATION OF DIFFERENT GALACTOLIPID MATERIALS

Lipid Class Analysis

Lipid class analysis was performed by high performance liquid chromatography, HPLC, using a column packed with diol-modified silica (LiChrosphere 100 DIOL, 5 μm, 250 mm×4 mm i.d.; E. Merck, Germany). The column was enclosed in a water bath held at 75° C. The analytical system consisted of a HPLC pump CM 4000 (LDC/Milton Roy, USA), and an injector, model 7125, with a 20 μl injection loop (Rheodyne Inc., USA). The evaporative light-scattering detector used was a Sedex 45 (S.E.D.E.R.E., France) equipped with a Sedex 55 nebulisation chamber with a drift tube temperature and air inlet pressure of 97° C. and 2.0 bar, respectively.

The flow of the mobile phase was 1 ml/min during the analysis. A binary solvent gradient, linear over 25 min, was used starting with 100% of A and ending with 100% of B, where A=hexane:isopropanol:n-butanol:tetrahydrofuran:isooctane:water, 64:20:6:4.5:4.5:1, and B=isopropanol:n-butanol:tetrahydrofuran:isooctane:water, 75:6:4.5:4.5:10. All solvents contained ammonium acetate, 180 mg/l.

Data collection and processing were done with GynkoSoft Data system version 4.22 (Softron GmbH, Germany). Typical amount injected for analysis was 100 μg. Identification was based on retention time comparison with authentic standards (Karlshamns Lipidteknik AB, Sweden). Volatile compounds were not detected in this system. Quantification was based on peak area calculations.

Zeta potentials were determined on dilute aqueous galactolipid dispersions with a Zetasizer 4 instrument (Malvern Instruments Ltd., UK)

TABLE 1

Characterisation of different galactolipid materials

|  | o-GL | o-h-GL | o-DGDG | w-GL | w-DGDG | r-GL |
|---|---|---|---|---|---|---|
| DGDG content, area % | 73 | 70 | 72 | 100 | 80 | 100 | 67 |
| Z-potential, mV | −74 | −76 | −30 | −51 | −75 | −38 | −37 |

In this Table 1 as well as in Table 2 below the following abbreviations are used o-GL=galactolipids from oats
o-h-GL=hydrogenated galactolipids from oats
o-DGDG=enriched galactolipids from oats
w-GL=galactolipids from wheat
w-DGDG=enriched galactolipids from wheat
r-GL=galactolipids from rye

FATTY ACID ANALYSIS

Analysis of the fatty acid profile was done by gas chromatography after transesterification of the lipids to fatty acid methyl esters. These were separated and quantified by capillary column gas chromatography on a Varian 3500 capillary Gas Chromatograph equipped with a capillary column 30 m×0.25 mm i.d. (DB-WAX; J&W Scientific, USA), an on-column injector and a flame ionization detector. Helium was used as the carrier gas. Integration was performed with GynkoSoft Data system version 4.22 (Softron GmbH, Germany). Transesterification was done by adding 1 mg of a lipid sample to 2 ml of dimethyl carbonate:isooctane, 1:1. 1 ml of a solution containing 2.3 g sodium dissolved in 200 ml of methanol was added and the test tube was shaken vigorously for 30 s and left at room temperature for 15 min to ensure complete reaction. 3 ml water was added and the test-tube was shaken and then centrifuged at 2×g. 0.5 μl of the organic layer was injected on the chromatograph with the following separation conditions. The oven was temperature programmed, starting at 130° C. (2 min), increased to 150° C. (30°/min) and 220° C. (3.2° C./min) with a 10 min hold. The injector temperature was 130° C. and the detector temperature was 250° C. Initially the gas flow was 2.7 ml/min. The results are expressed as normalized weight percentages using the external standard method. No correction factors are used for the minor constituents for which standards are not available or acceptably pure.

TABLE 2

Characterisation of fatty acid composition

| Fatty acid composition, weight % | o-GL | o-h-GL | o-DGDG | w-GL | w-DGDG | r-GL |
|---|---|---|---|---|---|---|
| C 14:0 |  |  |  |  | 1 |  |
| C 16:0 | 20 | 21 | 21 | 16 | 15 | 13 | 12 |
| C 18:0 | 1 | 1 | 74 | 2 | 1 | 1 |  |
| C 18:1 n-9 | 17 | 17 |  | 19 | 6 | 5 | 8 |
| C 18:1 n-7 | 1 | 1 |  | 1 | 1 | 1 | 1 |
| C 18:2 n-6 | 53 | 52 |  | 58 | 71 | 68 | 69 |
| C 18:3 n-3 | 2 | 2 |  | 3 | 3 | 3 | 5 |
| Minors <1% and unidentified | 6 | 6 | 5 | 1 | 3 | 8 | 5 |

NMR SPECTROSCOPY OF DIGALACTOSYLDIACYLGLYCEROLS

One-dimensional proton-decoupled natural abundance $^{13}C$ NMR spectra were recorded on a Bruker AM-400 spectrometer (Bruker Analytische Messtechnik GmbH., Germany) at a $^{13}C$ frequency of 100.614 MHz. The pulse angle was 36°, the pulse repetition time 1.0 s and resolution 1.526 Hz per data point. 3 Hz line broadening was applied during processing. The samples (10–40 mg) were diluted in a mixture of 730 μl DMSO-$d_6$ (Aldrich Chemical Comp., Inc., USA) and 20 μl $D_2O$ (Aldrich Chemical Comp., Inc., USA) and transferred to an NMR tube (5 mm i.d.).

TABLE 3

$^{13}C$ Chemical shifts (ppm) of digalactosyldiacylglycerols from wheat and oats

| Signal | w-DGDG | o-DGDG |
|---|---|---|
| Fatty acid moieties |  |  |
| C(n) | 13.8 | 13.7 |
| C(n-1) | 21.9 | 21.9 |
| C(n-2) | 30.8 | 30.8 |
| C, methylene | 28.3–28.9 | 28.4–29.0 |
| C, allylic | 26.5 | 26.5 |
| C, doubly allylic | 25.1 | 25.1 |
| C, olefinic | 127.6–129.6 | 127.6–129.5 |
| C3 | 24.3 | 24.3 |
| C2 | 33.3,33.5 | 33.3,33.5 |
| C1 | 172.2,172.5 | 172.1,172.4 |
| Glycerol moiety |  |  |
| sn-1 | 62.3 | 62.4 |
| sn-2 | 69.8 | 69.8 |
| sn-3 | 66.6 | 66.6 |

TABLE 3-continued $^{13}$C Chemical shifts (ppm) of digalactosyldiacylglycerols from wheat and oats

| Signal | w-DGDG | o-DGDG |
|---|---|---|
| Digalactosyl moiety | | |
| C1 (inner) | 103.6 | 103.6 |
| C1'(outer) | 99.4 | 99.4 |
| others | 60.4,66.3, | 60.4,66.3, |
| | 67.7,68.2, | 67.7,68.2, |
| | 68.6,69.3, | 68.6,69.3, |
| | 70.1,71.1, | 70.1,71.1, |
| | 72.8,72.8 | 72.8,72.9 |

EXAMPLE 1

Preparation of a Lipophilic Carrier (Enriched Evening Primrose Oil Containing 20% γ-Linolenic Acid (GLA))

A liphophilic carrier was prepared with the following ingredients:

| Ingredient | % |
|---|---|
| Galactolipid material | 50.0 |
| Enriched evening primrose oil, 20% GLA | 50.0 |

The galactolipid material was dispersed in the oil under high shear mixing at 22,000 rpm for 3 min. The oil phase was then kept at 50° C. for 40 min. A clear, highly viscous lipophilic carrier, which stayed clear upon cooling to room temperature, was obtained.

EXAMPLE 2

Preparation of a Lipophilic Carrier (Enriched Evening Primrose Oil Containing 20% GLA) Containing 5% Cyclosporine A.

A lipophilic carrier containing a pharmacologically active compound was prepared using the following ingredients.

| Ingredient | % |
|---|---|
| Galactolipid material | 19.0 |
| Enriched evening primrose oil, 20% GLA | 75.9 |
| Cyclosporine A | 5.1 |

The galactolipid material was dispersed in the oil under high shear mixing at 22,000 rpm for 2 min. The lipophilic carrier was heated to 50° C. and became clear. The cyclosporine A was added to the clear oil phase. The cyclosporine/oil mixture was kept at 50° C., with occasional shaking, until a clear liquid was obtained.

EXAMPLE 3

Preparation of a Lipophilic Carrier Containing Ascorbyl-6-GLA

A gel was prepared with the following ingredients:

| Ingredient | % |
|---|---|
| Ascorbyl-6-GLA | 6.25 |
| Galactolipid material | 40.72 |
| MCT oil | 53.03 |

Ascorbyl-6-GLA, the γ-linolenic acid ester of ascorbic acid (from Callanish Ltd., Scotland) was dispersed in the oil. The galactolipid material was added to the dispersion and the mixture was then heated to about 50° C. and submitted to high shear mixing. After cooling to room temperature, a viscous and slightly opaque stable dispersion was obtained.

EXAMPLE 4

Preparation of a Water-Free Disulfiram Formulations

A parenteral formulation with disulfiram, an alcohol deterrent, was made using the following ingredients:

| Ingredient | % |
|---|---|
| Galactolipids from oats | 20.0 |
| Disulfiram | 32.0 |
| MCT oil | 48.0 |

The ingredients were mixed using an ultraturrax homogeniser at 2000 rpm for 15 min and at 3000 rpm for 5 min.

This resulted in a suspension, containing a high amount of finely dispersed disulfiram particles, with a smooth and homogeneous consistency. The suspension showed excellent physical stability and no sedimentation could be observed during storage at room temperature. The viscosity of the suspension was relatively low and it was possible to deliver the formulation through a syringe equipped with a thin (i.d. 1.0 mm) needle.

The formulation is applicable for instillation into the duodenum in man, where it may act as a depot for disulfiram thus providing extended alcohol deterrent effect.

EXAMPLE 5

Preparation of Reverse Vesicles

Reverse vesicles were prepared using the following ingredients:

| Ingredient | Composition A % | Composition B % |
|---|---|---|
| Galactolipids from oats | 1.65 | 1.56 |
| Lysophosphatidylcholine from soybean | 0.40 | — |
| Phosphatidylinositol from soybean | — | 0.38 |
| Water | 0.56 | 0.64 |
| MCT oil | 97.39 | 97.42 |

After weighing the ingredients, the mixtures were sonicated in an ultrasonication bath for 1 h at 30°–40° C. The resulting fine dispersions were stable for more than a week. The presence of large reverse vesicles was evaluated with a differential interference phase contrast microscope (X2F-NTF-21; Nikon, Japan) with a video-enhanced system (Argus 10; Hamamatsu Photonics Co., Japan).

The reverse vesicles in this example are based on lipid ingredients, which are suitable for use in pharmaceutical and cosmetic applications. Previously, reverse vesicles have been prepared by using phospholipids or synthetic surfactants in hydrocarbon oil, the two latter ingredients normally being too toxic for human use. Furthermore, the reverse vesicles according to the present invention show a much better stability than previously reported for systems based on synthetic surfactants and hydrocarbon oil.

A reverse vesicle dispersion is an example of an organised solution in which bioactive materials, e.g. proteic drugs like interferons, and peptide hormones like calcitonin or insulin, may be incorporated. Incorporation of a water-soluble proteic drug or a hormone in a triglyceride oil by means of reverse vesicles may facilitate the transport of the drug across lipophilic cell membranes. The drug molecules are located within the bilayers of the reverse vesicles which have a stabilising effect on the drug. In particular, the drug may be protected from degradation in the gut when administered orally.

EXAMPLE 6

Preparation of Reverse Micelles

A highly viscous reverse micellar gel (organogel, microemulsion gel) was prepared in the following way:

| Ingredient | % |
| --- | --- |
| Galactolipids from oats | 17.9 |
| MCT oil | 81.3 |
| Water | 0.8 |

The gallactolipid material and the MCT oil were mixed together to form a homogenous dispersion. The water was added drop-wise to the dispersion under continuous magnetic stirring. A clear gel was formed almost instantly and maintained a high viscosity for over a month.

EXAMPLE 7

Preparation of a Microemulsion

A microemulsion was prepared with the following ingredients:

| Ingredient | % |
| --- | --- |
| Ascorbyl-6-GLA | 7.49 |
| Galactolipid material | 17.66 |
| MCT oil | 63.53 |
| Water | 11.32 |

Ascorbyl-6-GLA was dispersed in the oil. The galactolipid material was added to the dispersion. Warm membrane-filtered water was added to the oil phase under high shear mixing. This resulted in a clear, slightly yellowish and low-viscous liquid.

EXAMPLE 8

Preparation of a Water-in-Oil Emulsion

A water-in-oil emulsion was prepared with the following ingredients:

| Ingredient | % |
| --- | --- |
| Galactolipids from oats | 20.0 |
| MCT oil | 49.9 |
| 1.0% aqueous carrageenan gel | 30.1 |

The galactolipid material was mixed with the MCT oil to form a homogenous clear dispersion. The carrageenan gel, melted at 60° C., was added slowly to the oil-phase under high shear mixing. After cooling to room temperature, a high viscous, milky oil-continuous emulsion was formed.

We claim:

1. A lipophilic carrier preparation having a continuous lipid phase, comprising a polar lipid material in combination with a non-polar lipid, and optionally a polar solvent, wherein the polar lipid material is a galactolipid material consisting of about at least 50% digalactosyldiacylglycerols, and the remainder being other polar lipids.

2. A lipophilic carrier preparation according to claim 1, wherein the galactolipid material consists of about 70–80% digalactosyldiacylglycerols, and about 20–30% other polar lipids.

3. A lipophilic carrier preparation according to claim 1, wherein the galactolipid material consists of 100% digalactosyldiacylglycerols.

4. A lipophilic carrier preparation according to claim 1, wherein the galactolipid material is in an amount of about 1–50% by weight of the total preparation, and wherein the non-polar lipid in the remainder of the total preparation.

5. A lipophilic carrier preparation according to claim 1, wherein the preparation is in the form of reverse vesicles, comprising, by weight of the total preparation:

(a) a galactolipid material and optionally other amphiphiles in the amount of about 0.5–3.0% by weight;

(b) an aqueous solution in the amount of about 0.1–1.0% by weight; and (c) a non-polar lipid in the remaining amount of the total preparation.

6. A lipophilic carrier preparation according to claim 1, wherein the preparation is in the form of reverse micelles, comprising, by weight of the total preparation:

(a) a galactolipid material in the amount of about 1–50% by weight;

(b) an aqueous solution in the amount of about 0.1–5.0% by weight; and (c) a non-polar lipid in the remaining amount of the total preparation.

7. A lipophilic carrier preparation according to claim 1, wherein the preparation is in the form of water-in-oil emulsions, comprising, by weight of the total preparation:

(a) a galactolipid material in the amount of about 1–30% by weight;

(b) an aqueous solution in the amount of about 1–80% by weight; and (c) a non-polar lipid in the remaining amount of the total preparation.

8. A pharmaceutical, cosmetic or food product which comprises the lipophilic preparation of claim 1 as a carrier for an active substance.

9. A pharmaceutical composition comprising a lipophilic carrier preparation according to claim 1 and a bioactive substance.

10. A pharmaceutical composition according to claim 9, wherein the non-polar lipid is a triacylglycerol oil.

11. A method of orally, enterally, parenterally, rectally, vaginally, topically, ocularly, nasally or aurally administering to animals the pharmaceutical composition according to claim 9.

12. A method of preparing a lipophilic carrier preparation having a continuous lipid phase which comprises combining a polar lipid material with a non-polar lipid material,
   wherein the polar lipid material is a galactolipid material consisting of about at least 50% digalactosyldiacylglycerols, and the remainder being other polar lipids.

13. A method according to claim 12 wherein the galactolipid material consists of about 70–80% digalactosyldiacylglycerols, and about 20–30% other polar lipids.

14. A method according to claim 11 wherein the galactolipid material consists of 100% digalactosyldiacylglycerols.

15. A method of preparing reverse vesicles which comprises combining a galactolipid material consisting of about at least 50% digalactosyldiacylglycerols, other polar lipids and, optionally phospholipids or other amphiphiles.

16. A method according to claim 15, wherein the galactolipid material consists of about 70–80% digalactosyldiacylglycerols, and about 20–30% other polar lipids.

17. A method according to claim 15, wherein the galactolipid material consists of 100% digalactosyldiacylglycerols.

18. A pharmaceutical composition according to claim 10, wherein the triacylglycerol oil is selected from the group consisting of a medium-chain triacylglycerol oil, evening primrose oil, a palm oil function, and bioactive substance.

* * * * *